(12) United States Patent
Laverack et al.

(10) Patent No.: US 11,420,201 B2
(45) Date of Patent: Aug. 23, 2022

(54) COMPACT TESTING DEVICE

(71) Applicant: SPD Swiss Precision Diagnostics GMBH, Geneva (CH)

(72) Inventors: Paul J. Laverack, Leighton Buzzard (GB); James Gani, Bedford (GB)

(73) Assignee: SPD Swiss Precision Diagnostics GMBH, Geneva (CH)

( * ) Notice: Subject to any disclaimer, the term of this patent is extended or adjusted under 35 U.S.C. 154(b) by 211 days.

(21) Appl. No.: 16/598,744

(22) Filed: Oct. 10, 2019

(65) Prior Publication Data

US 2020/0114348 A1 Apr. 16, 2020

(30) Foreign Application Priority Data

Oct. 10, 2018 (GB) ...................................... 1816559

(51) Int. Cl.
*B01L 3/00* (2006.01)

(52) U.S. Cl.
CPC ....... *B01L 3/5023* (2013.01); *B01L 2200/087* (2013.01); *B01L 2300/025* (2013.01); *B01L 2300/046* (2013.01)

(58) Field of Classification Search
CPC ............. B01L 3/5023; B01L 2200/087; B01L 2300/025; B01L 2300/046; B01L 3/5055;
(Continued)

(56) References Cited

U.S. PATENT DOCUMENTS

| | | |
|---|---|---|
| 2004/0017113 A1 | 1/2004 | Xing et al. |
| 2004/0171173 A1* | 9/2004 | Eckermann .......... B01L 3/5023 436/514 |

FOREIGN PATENT DOCUMENTS

| | | |
|---|---|---|
| CN | 205450001 U | 8/2016 |
| EP | 0716305 A1 | 6/1996 |

(Continued)

OTHER PUBLICATIONS

Merriam Webster definition of "hinge" retrieved using the WayBack Machine from Mar. 11, 2016 https://web.archive.org/web/20160311154044/https://www.merriam-webster.com/dictionary/hinge (Year: 2016).*

(Continued)

*Primary Examiner* — Matthew D Krcha
*Assistant Examiner* — Sophia Y Lyle
(74) *Attorney, Agent, or Firm* — Foley Hoag LLP; Erik A. Huestis (57) ABSTRACT

A lateral flow testing device includes a main body adapted to support an element for collecting a sample. The element is supported at a distal end of the testing device and is in fluid communication with one or more testing components having an analyte detection zone for detecting one or more analytes present in said sample. The testing components produce visual information related to said sample, thereby informing the user of the outcome of a test. The device incorporates a handle reconfigurable with respect to said main body such that in a first handle configuration, the handle hinders sight of the visual information to improve privacy of the test, and in a second handle configuration, the handle facilitates the collection of said sample by increasing a distance between a proximal end of the testing device and the element.

28 Claims, 6 Drawing Sheets

(58) Field of Classification Search
CPC ....... B01L 2200/185; B01L 2300/0825; A61B 2010/0006; A61B 10/0045; A61B 10/0051; A61B 10/007; A61B 10/0012; G01N 33/54366
See application file for complete search history.

(56) References Cited

FOREIGN PATENT DOCUMENTS

| | | | | |
|---|---|---|---|---|
| EP | 716305 B1 | * | 9/1999 | ....... G01N 33/54366 |
| EP | 2542160 A1 | | 1/2013 | |
| JP | 07120467 A | * | 5/1995 | |
| JP | H07120467 A | | 5/1995 | |
| JP | 3753282 B2 | | 3/2006 | |
| JP | 2006/266764 A | | 10/2006 | |
| WO | WO-97/26083 A1 | | 7/1997 | |
| WO | WO-2006/010113 A2 | | 1/2006 | |

OTHER PUBLICATIONS

Combined Search and Examination Report for Application No. GB1816559.7 dated Apr. 5, 2019.
Written Opinion of International Application No. PCT/EP2019/077543 dated Feb. 10, 2020.

* cited by examiner

COMPACT TESTING DEVICE

CROSS-REFERENCE TO RELATED APPLICATIONS

This application claims the benefit of United Kingdom Application No. 1816559.7, filed Oct. 10, 2018, which is hereby incorporated by reference in its entirety.

TECHNICAL FIELD

The present invention relates to a testing device for collecting a sample and then testing it in situ, ie on the device, so that the outcome of the test is made available on the device to a user immediately or shortly after the collection of the sample.

More particularly, the present invention also relates to a lateral flow testing device, ie a testing device in which a sample collection element is in fluid communication via a flow path with one or more testing components for testing the sample based on the presence or absence of one or more target analytes.

More particularly, the present invention also relates to a portable and/or consumable lateral flow testing device, such as a disposable, single-use lateral flow testing device.

The sample can be urine, amongst others, and testing can be for pregnancy or other conditions such as ovulation, menopause etc, such as, but not exclusively, in human beings.

The present invention also relates to associated methods and kits.

BACKGROUND

Various diagnostic consumer products are known which analyse a fluid sample, such as urine, saliva or blood to determine the presence and/or amount of one or more analytes. These may be small, handheld devices used by first applying the biological sample to an absorbent pad. The devices are configured subsequently to convey the fluid along a flow path to internal testing components without needing any significant gravitational encouragement, eg by capillary action, or user-applied pressure, where certain reactions take place to produce a test result. The test result can then be instantly read by the user.

US 2004/0171173 A1 discloses a compact testing device for collecting liquid samples such as saliva comprising an absorbent pad and two housing parts which are connected to the absorbent pad in a movable manner and can enclose the absorbent pad.

EP 0716305 A1 discloses a compact testing device for executing a pregnancy test by registering the presence of hCG hormone in urine with a test strip held between two layers forming a housing made of cardboard, paper or other material with a lignocellulose content.

Accordingly, there is a need to provide compact testing devices having improved or alternative mechanical arrangements with respect to the prior art. The present disclosure concerns one or more desirable mechanical arrangements particularly suited to these compact testing devices.

The present disclosure does not concern the bio-chemistry or physics underlying the testing devices as such, although basic information relating to said bio-chemistry and/or physics is herein referenced to provide suitable general background for the understanding of the present invention, at least in connection with lateral flow testing devices.

Similarly, the present disclosure does not focus on the testing and/or reading technologies used by these devices.

The mechanical arrangements described herein are useable in connection with qualitative and/or quantitative test reading technologies, whether based on direct visual inspection by the user or on more sophisticated test reading by readings means integral to the device, or by interfacing equipment such as optical readers or other types of information interpreters or interfaces, such as displays, insofar as the test output is made available in situ, ie on the device. It is not necessary, however, that the test output be made available only on the device. It could in addition be made available elsewhere, for example on a personal computer or mobile phone device in communication (for example via Bluetooth® or other connection protocol) with the testing device, provided that the testing device include appropriate transmission means capable of transmitting the information.

SUMMARY OF INVENTION

The present disclosure provides in an aspect a testing device comprising:

a main body adapted to support an element for collecting a sample, said sample collection element being supported at a distal end of the testing device and being in communication, optionally via a flow path, with one or more testing components provided within said main body for producing visual information related to said sample, said one or more testing components optionally comprising an analyte detection zone for locally detecting one or more predetermined analytes contained in said sample; and, a handle reconfigurable with respect to said main body such that in one or more first handle configurations the handle hinders sight of the visual information, and in one or more second handle configurations the handle facilitates the collection of said sample by increasing a distance between a proximal end of the testing device and the sample collection element;

wherein the testing device is adapted such that the handle is reconfigurable from at least one of said second handle configurations to at least one of said first handle configurations to hinder (at least partially, or, optionally, totally) the sight of the visual information after that said testing has been carried out.

Described herein is therefore a testing device that is practical and user-friendly, and that in addition advantageously helps to keep the test discreet and private, for example in case the compact testing device is disposed of after that testing has taken place.

The compact size of the testing device also advantageously reduces the size of the packaging and hence reduces potential waste.

In preferred embodiments, the main body is elongated and defines a longitudinal direction along which the device extends.

The sample collection element and the one or more testing components may be organised on said device so as to be spaced apart along said longitudinal direction.

The testing components may be usefully located proximally on the elongated body relative to the sample collection element which may instead be located distally relative to the testing components.

The sample collection element and the one or more testing components may be adjacent.

In preferred embodiments, the sample collection element and the one or more testing components are contiguous, for example they may be in direct contact one with the others as it is the case with lateral flow testing devices.

The sample collection element and the one or more testing components may be over- or under-lapping at least partially one with the others, or adjoining one against the others, for example in the longitudinal direction defined by the elongated main body of the testing device.

The handle may also extend substantially in said longitudinal direction; this may be the case in at least one of said first and/or at least one of said second configurations.

In preferred embodiments, the handle or a main portion thereof extends substantially parallel or at a small angle (for example about 15 degrees) to the longitudinal direction defined by the elongated main body of the testing device when the handle is in an extended, second configuration.

In preferred embodiments, the handle or a main portion thereof extends substantially parallel to said longitudinal direction when the handle is in a retracted, first configuration.

In preferred embodiments, the handle (or main portion thereof) substantially extends in said longitudinal direction defined by the elongated main body of the testing device in one preferred first configuration so that it substantially lies over or overlaps said elongated main body. The handle may lie generally parallel to said elongated main body in this preferred first configuration. The preferred first configuration may be a folded or retracted configuration for the handle that maximises the compactness of the testing device, and this can be, for example, for storing away the device and/or for disposing of the device.

In preferred embodiments, the handle (or main portion thereof) also substantially extends in said longitudinal direction in one preferred second configuration so that the handle effectively acts as an extension of the device in the longitudinal direction. The preferred second configuration may be a deployed or extended configuration for the handle, and this can be, for example, an ergonomic configuration that facilitates collection of the sample.

Alternatively or additionally, the angle formed by the handle and the main body of the device when the handle is in a second configuration could be variable, and changeable or settable by the user, so that the user can change and set this angle to their preferred values so as to maximise or adjust the aid provided by the device in the collection of the sample.

The handle may be rotatably coupled with respect to the main body of the device.

Accordingly, reconfiguration of the handle between first and second configurations, or between second and first configurations, as the case may be, such as the above preferred first and second configurations, may be across about 180 degrees, or half a turn, or less than that.

The handle may be rotatable in-plane or in out-of-plane directions with respect to a plane over which the main body of the testing device generally extends. However, other more complex configurations may also be possible.

Considering 0 degrees a reference position for the handle (or main portion thereof) when folded towards or upon the body of the testing device for hindering the visual information, for example in the preferred configuration mentioned above, the handle may be reconfigured across about 180 degrees, about 175 degrees, about 170 degrees, about 165 degrees, about 160 degrees, about 155 degrees, about 150 degrees, about 135 degrees, or less, from the reference position to a second configuration.

The handle (or main portion thereof) may be not completely folded over or upon the main body of the testing device when the handle is in the reference first configuration. Accordingly, the "0 degrees" reference position described in the paragraph above may be in relation to a reference first configuration with the handle (or main portion thereof) forming, for example, an angle of about 10 degrees, about 20 degrees, about 30 degrees or about 45 degrees with respect to the main body of the testing device and/or the longitudinal direction along which it extends and/or the plane over which it lies or that it defines.

The sample collection element may comprise an absorbent pad, or wick.

The one or more testing components may comprise one or more fluidly communicating porous strips.

The testing components may comprise optical reading electronics adapted to read said visual information and output enhanced and/or interpreted and/or interfaced and/or displayed and/or visual information. Alternatively or in addition, said electronics may output aural information relating to the outcome of the test.

In at least one of said first handle configurations, the handle may completely impede sight of the visual information produced by the test. This may for example be the case when the handle fully overlaps the main body, or fully covers the main body of the testing device in its folded configuration.

The main body of the device may define a window for displaying said visual information. Accordingly, the handle may fully overlap with, or fully cover, said window to impede sight of the visual information.

As described above, in preferred embodiments, there is defined between the one or more first handle configurations a designated handle configuration that maximises compactness of the testing device for storage, transportation and/or disposal. This can be, for example, the configuration with the handle fully overlapping the body of the device and the window which may have an opening on an upper face of said body. This designated first configuration may in principle be distinct from other one or more first configurations still suitable for hindering the sight of the visual information from said window.

In preferred embodiments, the handle and the main body are moveable, such as being rotatable, one with respect to the other via a hinge.

The hinge may be formed by the arrangement of the handle and the main body of the testing device (that is the hinge is formed directly by coupling the handle and the main body), or it may comprise an additional hinge member which is not part of the handle and/or main body of the device as such.

Alternatively, the handle may be slidingly coupled to the body of the device. For example, the sliding coupling of the handle and the main body of the testing device may be via one or more rails, guides or similar linear coupling elements located as appropriate on the body and/or on the handle.

Alternatively, the handle and the body may be obtained from a single sheet of an appropriate deformable material, such as a plastic or cardboard sheet, with one or more suitable weakness points, such as fold-lines or the like.

Alternatively, the handle may be formed as a sleeve for receiving the main body of the test device there within.

In preferred hinged embodiments, the handle may be connected at a proximal end portion of the main body of the device via said hinge.

The hinge may define a hinge axis transversal with respect to the main body, and/or relative to the longitudinal direction defined by the elongated main body of the testing device.

The hinge and/or hinge axis may be longitudinally distally offset with respect to a proximal edge of the main body of the device. The offset could be one or more millimetres or one or more centimetres, or fractions thereof.

The hinge axis may lie coplanar with a nominal plane on which the main body may generally lie.

The hinge may comprise one or more hinge pins provided on the main body of the device.

The handle may comprise one or more associated hinge seats.

Embodiments in which the hinge pins are provided on the handle and the hinge seats on the main body of the device are however also possible.

Other manners of implementing the hinge may be devised in addition to the hinge member mentioned above, for example by providing a spherical hinge, such as a hinge comprising a ball joint.

In preferred embodiments, retention means for retaining the handle in one or more of said first and/or second configurations are provided.

Further, the handle may be retained in any one of a discrete number of positions, or at any position within a range of possible positions, depending on the specific arrangement and functionality of the retention means.

Whilst such retention means may come in many different forms, in preferred embodiments the retention means comprise a handle retaining mechanism.

In preferred hinged embodiments, the handle retaining mechanism comprises an aperture or indentation, for example in the form of a slot, defined on said main body, and a protrusion, provided on said handle, for engaging with said aperture, indentation or slot when the handle is in one of said first and/or second, preferably second, configurations. Such engagement may generate a retention force. The retention force may be overcome by the user to reconfigure the handle. The handle may therefore be substantially freely moveable, and therefore reconfigurable, between a first and a second configuration, before it is retained in place.

The protrusion and the aperture, indentation or slot may be configured such that the protrusion snap-fits in place into the aperture, indentation or slot when the handle is in a required first and/or second configuration. For example, said required configuration may be a second configuration with the handle fully extended to increase the length of the device in preparation for sample collection and testing whilst improving the ergonomics of handling the device.

Vice versa, the protrusion may be formed on the body of the device and the aperture, indentation or slot may be defined on the handle.

In embodiments where the user may set the angle formed between the handle and the main body of the device, the retention means and/or mechanism may be adapted to retain the handle in one or more discrete or continuous retention positions, such as angular positions, between two limit retention positions corresponding, respectively, to a first and a second configuration for increasing the ergonomics of the sampling operations carried out by the user.

A set of radial recesses may be formed on the hinge pins and an inwardly extending radial locating projection may be formed on each of the hinge seats for locating into any of said radial recesses, thereby retaining the handle in any of a discrete number of allowed angular positions.

Alternatively, friction between the hinge pins and corresponding seats may be suitable to retaining the handle in any of an infinite range of positions between two limiting angular positions.

The handle retaining mechanism may be arranged as an over-centre mechanism.

The retention means or mechanism may comprise one or more additional securing features for securing the handle in place in one or more specified or required first and/or second configurations. Accordingly, the handle may no longer be reconfigurable while such additional securing features operate.

Said securing features may be applicable to and/or removable from the testing device. As such, these features would not per se be part of the device. However, they may be provided in addition or as a complement to the testing device. For example, the external retention features may comprise one or more retention pins, belts, buckles, elastic bands, clips or the like.

The handle retaining mechanism may be adapted to release or unlock the handle for reconfiguration when a predetermined force, for example a force that tends to rotate the handle around said hinge greater than a predetermined threshold, is exerted on the handle retaining mechanism.

The handle retaining mechanism may comprise a key for locking and/or unlocking the handle so that the handle may or may not be reconfigured unless the key is first operated to unlock the handle retaining mechanism. Said key may be for example in the form of a pin, pusher, slider, button or the like.

The handle may be reconfigurable with respect to the main body in at least one of said one or more first handle configurations to obstruct collection of the sample.

In a folded or retracted configuration, the handle may overlap or lie over at least a portion of the sample collection element, or absorbent wick or pad, to discourage sample collection when the handle is in such a first configuration.

In preferred embodiments, the length of the handle is greater than, or at least substantially equal to, a distance between i) the hinge, and/or the proximal end of the main body of the test device, and ii) the visual information, and/or said window defined on the main body of the device.

In non-hinged embodiments, other arrangements would however be possible, for example involving a shorter handle.

The main body of the device may be further adapted to support a cap for covering and/or protecting the sample collection element. Accordingly, in certain embodiments the test device comprises said cap. Accordingly, the handle may be such that in at least some of said first configurations it covers said cap, for example by way of overlapping or lying over said cap or portion thereof. The handle may in at least one of said first configurations partially overlap the cap, preferably longitudinally. Accordingly, the overall longitudinal length of the device in a folded configuration, such as a packaging configuration, may be solely dictated by the main body and the cap. The handle may thus marginally contribute solely to added overall thickness of the device (compared to a device without reconfigurable handle), but not to added overall length in said at least one of said first configurations. This maximises the compactness of the capped testing device, at least in the longitudinal direction, while providing a reconfigurable handle to perform added functions.

Preferred embodiments of the testing device are lateral flow testing devices which, for their own nature, have an architecture which lends itself particularly well to the mechanical arrangements disclosed herein.

The sample collection element and the testing components may be in fluid communication via a flow path.

The testing components may comprise an analyte detection zone for detecting analytes contained in said sample.

The one or more testing components may comprise mobilizable dried particulate labels for bindingly reacting with said analytes.

The sample may be urine, amongst other options such as blood and/or saliva.

The testing device may be a pregnancy and/or ovulation and/or menopause testing device.

According to a further aspect of the present disclosure, there is provided a disposable testing device comprising a testing device as described herein.

The sample collection element and the testing components may be permanently mounted to, on, within or in the main body.

The main body may be a monolithic component or a multiple part component such as a two-part component.

The two-part component may comprise upper and lower shell-like parts. These parts may be made, for example, of a thin but substantially rigid plastic material.

The sample collection element may be sandwiched between said upper and lower parts.

The testing components may be accommodated within an inner space or cavity defined by said upper and lower parts.

According to a further aspect of the present disclosure, there is provided a kit of assemblable parts for assembling a testing device according to any one of the aspects of the disclosure described herein.

According to yet a further aspect of the present disclosure, there is provided a method of testing a sample, the method comprising:
  providing a testing device comprising:
    a main body adapted to support an element for collecting a sample, said sample collection element being supported at a distal end of the testing device and being in communication with one or more testing components for producing visual information related to said sample, and,
    a handle reconfigurable with respect to said main body such that in one or more first handle configurations the handle hinders sight of the visual information, and in one or more second handle configurations the handle facilitates the collection of said sample by increasing a distance between a proximal end of the testing device and the sample collection element;
  moving the handle to a second handle configuration in preparation for carrying out said testing;
    collecting a sample;
    moving the handle to a first handle configuration to hinder (at least partially, and, optionally, totally) sight of the visual information after that said testing has been carried out.

The method may further comprise overcoming a force generated by a handle retaining means or mechanism as described herein for reconfiguring the handle in one of said first or second configurations, as the case may be.

Features described herein in connection with any of the aspects of the present disclosure are to be assumed readily combinable or readily adaptable to be combinable with any other aspects of the present disclosure, unless specifically stated otherwise.

BRIEF DESCRIPTION OF THE SEVERAL VIEWS OF THE DRAWINGS

The invention will now be described purely by way of example with reference to one or more embodiments thereof, as illustrated in the attached drawings in which:

FIGS. 9A-I show a sequence of perspective views of the compact testing device of FIGS. 1-8 from the rear, illustrating the reconfiguration of the handle of the testing device from a first, storage configuration to a second, test-ready configuration as described herein.

DESCRIPTION

The present inventors have realised that lateral flow testing devices have an architecture which lends itself particularly well to the mechanical arrangements described herein. As a result, lateral flow testing devices incorporating one or more of the mechanical arrangements described herein are practical, user-friendly, yet help to keep the outcome of the test private, as it will be further discussed below.

The advantages associated with the mechanical arrangements described herein can however be extrapolated to compact testing devices more generally than lateral flow testing devices, insofar as such testing devices have a sample collection element and are also provided with testing components for producing a test result in situ, ie on the testing device itself, ready for visualisation from a user of the compact testing device.

Figure 1:
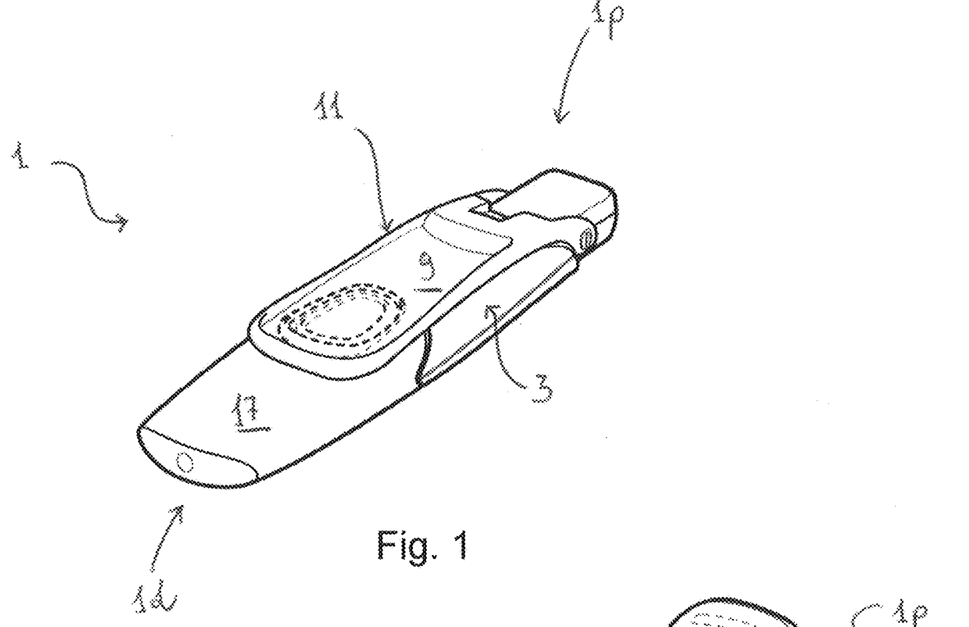
FIG. 1 is a perspective view from the front of a compact testing device in accordance with an embodiment of the present invention in a first, storage configuration.

Accordingly, with reference to FIG. 1 there is illustrated an example of a compact testing device 1 comprising the mechanical arrangements described herein. The described testing device 1 is in the form of a lateral flow pregnancy test 1.

The device 1 includes a main body 3 adapted to support an element 5 for collecting a urine sample 100. The sample collection element 5 is not visible in FIG. 1 since a cap 17 is applied to the testing device 1. The cap 17, which is provided separately from the provision of a reconfigurable handle 9 (this will be further described below) also supported on the main body 3 of the device 1 just like the cap 17, protects the sample collection element 5 before use, and upon unpacking the device 1 may signal to the user, together with the handle 9 in the position shown in FIG. 1, that the testing device is unused and thus ready to receive a sample. The sample collection element 5, which in the presently described embodiment is an absorbent wick 55, is shown for example in FIGS. 3 and 4, where the sample 100 is also schematically represented by thickened arrows.

Figure 3:
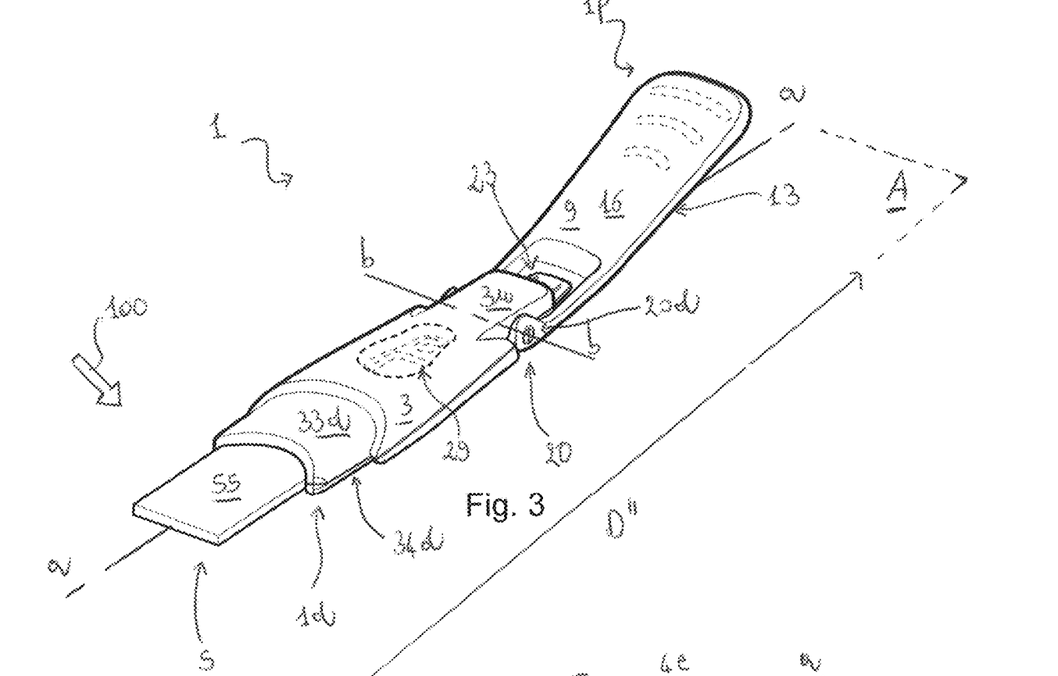
FIG. 3 is a perspective view from the front equivalent to that of FIG. 2, with a cap of the testing device removed to reveal a collection wick in preparation for a sample collection operation.
Figure 4:
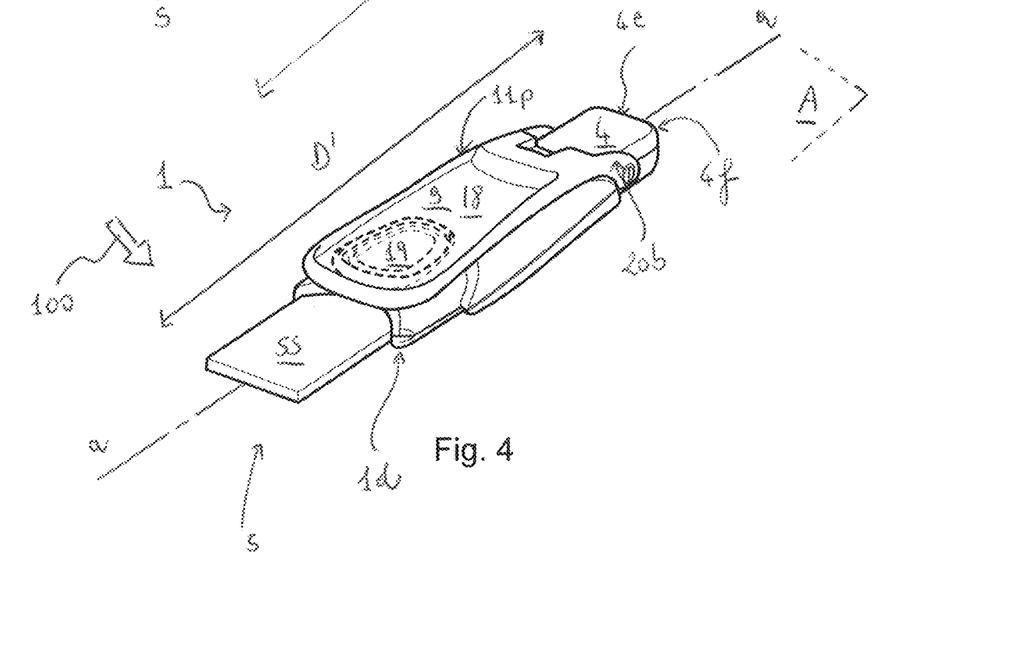
FIG. 4 is a perspective view from the front equivalent to that of FIG. 3, with a handle of the testing device folded in preparation for disposing of the device.

The sample collection element 5 is supported at a distal end 1d of the testing device 1 as best shown, for example, also in FIGS. 3 and 4. In the described compact testing device 1, the absorbent wick 55 is cantilevered from said main body 3. However, this needs not always be the case. For example, the sample collection element 5 could be provided as an element bridging two respective portions of the main body 3 of the device (this arrangement is not shown), or it could be otherwise supported. For example, it could be provided so as to be supported on a surface of the main body 3 of the testing device 1.

So that testing can be performed, the sample collection element 5 is in fluid communication with one or more testing components 7 provided together with the testing device 1. In the described arrangement, the testing components 7 are disposed within the main body 3 of the testing device 1, which defines internally a space or cavity for accommodating the same. A small portion of the testing components 7 is visible in FIG. 7A.

The testing components 7 are responsible for producing visual information 200 that will constitute the result of the test to be carried out. The visual information 200 in the presently described pregnancy test 1 is in the form of one or more coloured bars, shown schematically also in FIG. 7A. It will be appreciated that, in general, the visual information 200 may be qualitative or quantitative (or both) and will relate to certain properties of the sample 100.

In the described testing device 1, the visual information 200 is qualitative and relates to the presence (or absence) of the "human Chorionic Gonadotropin" (hCG) hormone in the tested urine 100. The pregnancy test 1 thus informs the user very shortly after the sample 100 has been collected as to the presence (or absence) of a pregnancy.

As mentioned above, a handle 9 is provided at the opposite end 4 of the main body 3 of the testing device 1 with respect to the sample collection element 5. The handle 9 is reconfigurable with respect to said main body 3 between at least one first configuration 11 and at least one second configuration 13.

In any of said first configurations 11, the handle at least partially hinders, obstructs or impairs sight of the visual information 200.

Figure 9A:
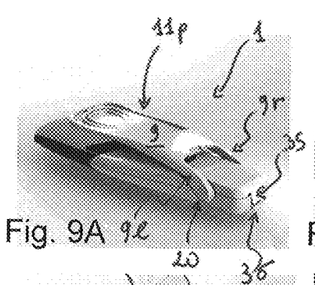
Figure 9B:
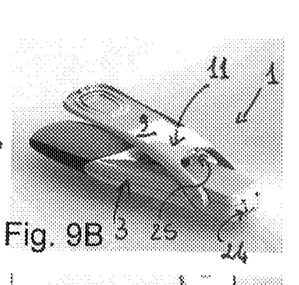
Figure 9C:
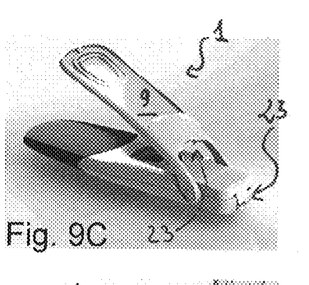
Figure 9D:
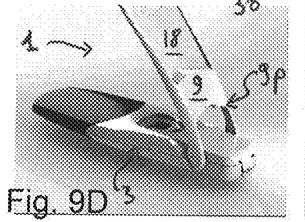
Figure 9E:
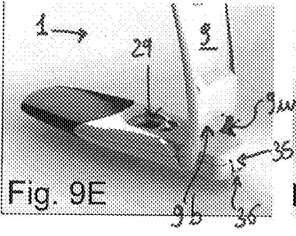
Figure 9F:
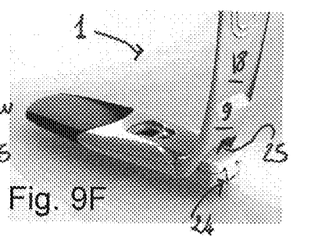
Figure 9G:
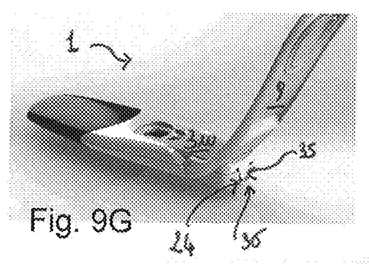
Figure 9H:
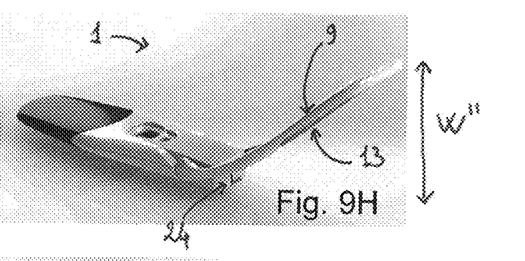

In any of said second handle configurations 13, the handle 9 facilitates the collection of said sample 100 by increasing a distance D" between the proximal end 1p of the testing device 1 (the part of the instrument that is gripped by the user to collect the sample 100) and the sample collection element 5. As is clear from FIG. 3, the proximal end 1p of the device 1 is further spaced from the sample collection element 5 than in the arrangement of FIG. 1 or 4, where the handle 9 is folded. In FIG. 4, the distance referred to above is denoted D' and D' is less than D". Other metrics to define the ergonomics of the handle (ie the degree of help it provides to the user) could however be used. For example, the handle 9 may be retained in a second configuration 13 in the position illustrated in FIG. 9H rather than in the position shown in FIGS. 6 and 9I. In the position of FIG. 9H, the maximum transversal width W' of the testing device 1 is greater than the maximum transversal width W' illustrated in FIGS. 6 and 9I, or the maximum transversal width W of the device in the compact configuration of FIGS. 5 and 9A. Parameter W could constitute an appropriate metrics. Alternatively, an appropriate metrics for quantifying the ergonomics of the testing device could be a combination of the parameters D and W.

Figure 2:
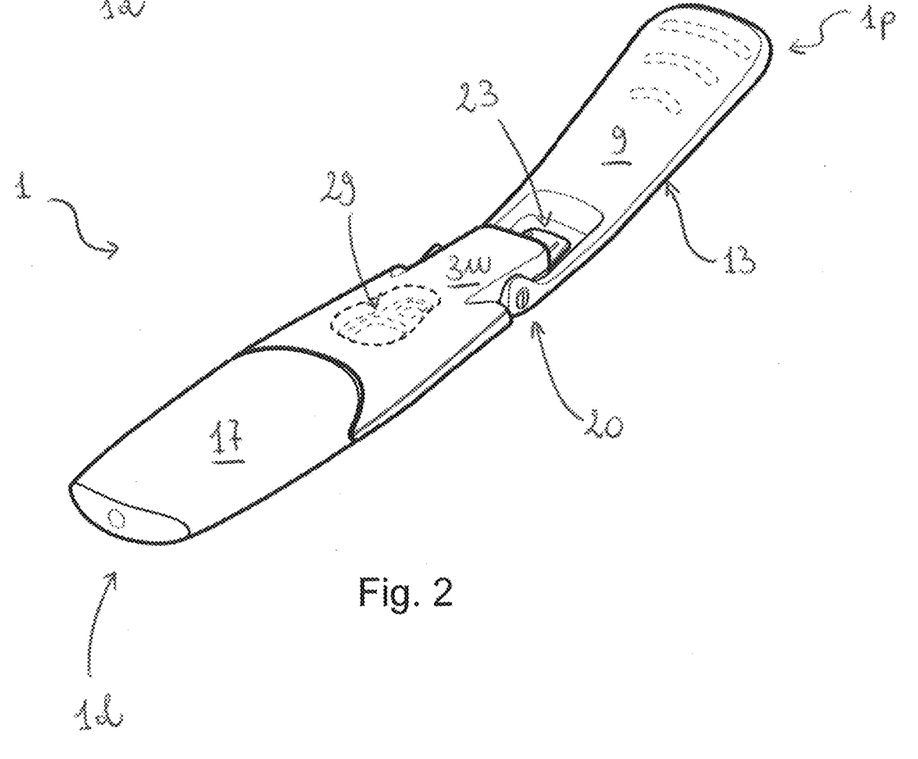
FIG. 2 is a perspective view from the front of the testing device of FIG. 1 in a second, extended configuration.

Once the sample 100 has been obtained and applied to the sample collection element 5, and the test has been carried out by the testing components 7, the handle 9 can be reconfigured from the second handle configuration 13 shown in FIGS. 2 and 3 to the first handle configuration 11 of FIG. 4 to hinder sight of the visual information 200, thereby increasing privacy for the user. The user is therefore less exposed to the information 200 becoming accidentally discovered. The user may for example wish to dispose of the pregnancy test 1 whilst having increased assurance that the information 200 will not accidentally be revealed to an occasional onlooker.

The described pregnancy test 1 has an elongated main body 3 which extends along a longitudinal direction a-a as best shown in FIGS. 3-6. As it can be appreciated from FIG. 3, the sample collection element 5 and the testing components 7 are disposed along said longitudinal direction a-a one next to the others. Since the testing device 1 described here is a lateral flow device, the absorbent wick 55 and the testing components 7 are in fluid communication so that at least a portion of the sample 100 can fluidly reach an analyte detection zone 201 provided as part of the testing components 7 (reference is made to FIG. 7A). In the analyte detection zone 201, certain reagent labels are capable of reacting with the analyte in question (the hCG hormone in the case of the described pregnancy test 1) and then become visible to the user at a desired location where they accumulate to provide the visual information 200.

In principle, the mechanical arrangements described herein are equally applicable to non-lateral flow architectures insofar as the sample collecting element 5 and the onboard testing components 7 can exchange the sample so that testing can be performed, and the test result can be made available in the form of visual information on the device 1.

The sample collection element 5 and the testing components 7 may be spatially arranged according to various architectures. It is not the purpose of the present disclosure to describe in detail such architectures. However, in the present example the sample collection element 5 has an inboard end overlapping and in fluid contact with a porous strip which is part of the testing components 7. The porous strip is in fluid communication with an analyte detection member, which is also part of the testing components 7. The analyte detection member is where the analyte detection zone 201 is located and detects the analytes if present in the sample 100. Accordingly, the sample collection element 5 and the testing components 7 are in this device 1 contiguous and in direct contact one to the others. However, different arrangements are possible.

Figure 5:
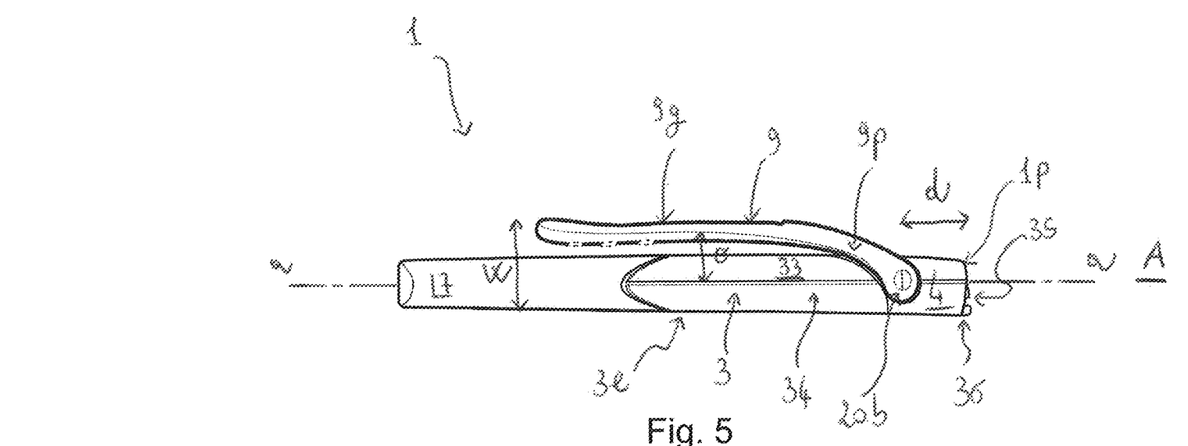
FIG. 5 is a side elevation of the compact testing device in the configuration of FIG. 1.
Figure 6:
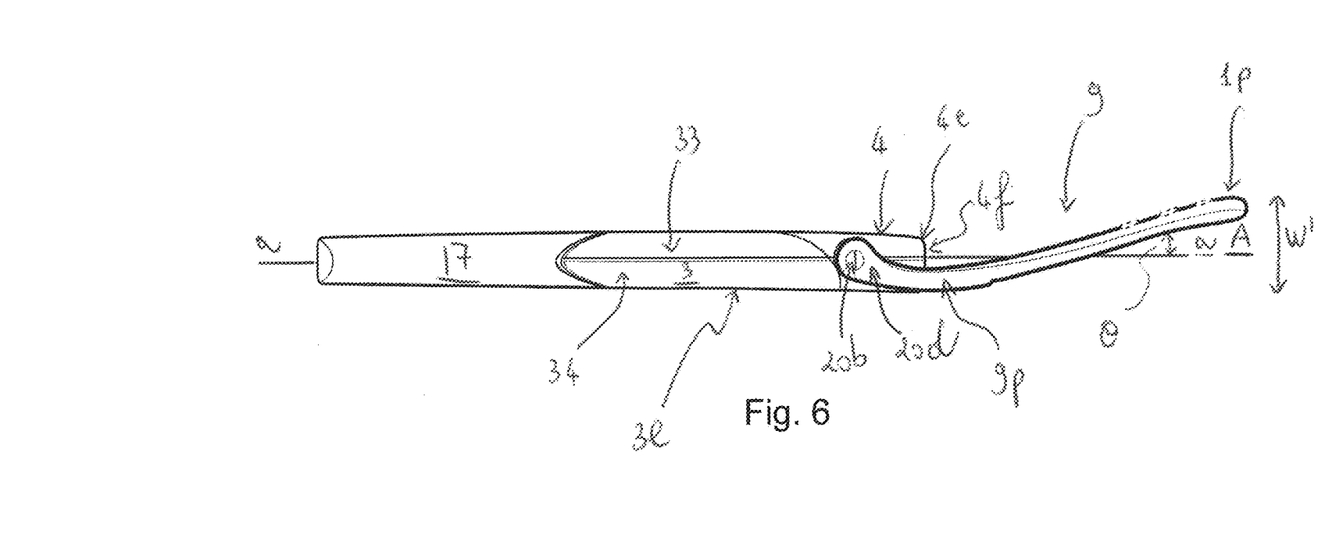
FIG. 6 is a side elevation of the compact testing device in the configuration of FIG. 2.
Figure 10:
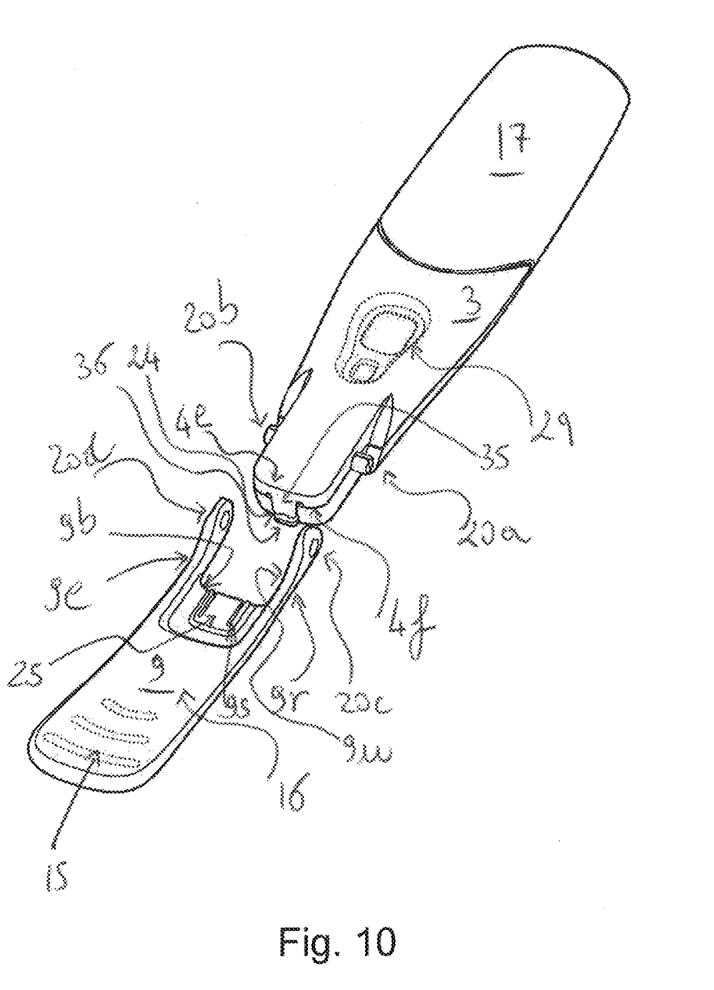
FIG. 10 is an exploded perspective view of the testing device showing the handle and the main body separated.

As best appreciated with reference to FIGS. 5, 6 and 10, the handle 9 can be divided into two parts: a relatively straight gripping portion 9g and a relatively curved pivoting portion 9p. The gripping portion 9g extends substantially longitudinally along the direction a-a both in the folded first configuration 11 and in the extended or deployed second configuration 13. The gripping portion 9g of the handle 9 is provided with three ridges 15 on the handle's inner side 16 and with concentric, generally annular protruding gripping elements 19 on the handle's outer side 18. However, this needs not always be the case. In alternative embodiments, for example, the ridges 15 and gripping elements 19 could be exchanged with one or more concave features such as indentations or the like. The indentations may have any suitable shapes. Likewise, the ridges 15 and protruding gripping elements 19 may have a range of alternative but still suitable shapes.

In more detail, it can be observed that the gripping portion 9g of the handle 9 in the folded configuration is generally parallel and slightly offset by a distance "o" with respect to a notional plane A over which the main body 3 of the testing device 1 lies (see FIG. 5). The plane A is represented schematically also in FIGS. 3-6.

The gripping portion 9g of the handle 9 forms an angle of about 15 degrees with the plane A when the handle 9 is in the extended configuration, as shown in FIG. 6. As apparent, the handle 9 still has an extension along direction a-a although it has an inclination with respect to plane A and/or direction a-a.

Any configuration of the handle 9 that increases the distance between the proximal end 1p of the testing device 1 (relative to the configuration of the testing device 1 with the handle 9 fully closed, for example) and the sample collection element 5 can be considered as a possible, advantageous second configuration 13 for the handle 9 described herein (although, as mentioned above, alternative metrics are possible). With the handle 9 in a second configuration 13, the collection of the sample 100 is facilitated. As it will be further described below, certain one or more second configurations 13 may be particularly advantageous as they increase the ergonomics of the test device 1.

Similarly, any configuration 11 of the handle 9 that at least partially hinders, obstructs or impairs the sight of the visual information 200 can be considered as a possible, advantageous first configuration 11 for the handle 9. With the handle 9 in a first configuration 11, the visual information 200 is made more difficult or impossible to be viewed.

Accordingly, there are at least in principle defined a number, even infinite, of first and/or second configurations for the handle 9, and not only those shown for example in FIGS. 1-6—these instead only representing preferred first and second configurations. So, for example, with reference to FIG. 9, the handle 9 in the configuration shown in FIG. 9H may still represent a suitable second configuration 13 within the purposes of the present disclosure. Likewise, the handle 9 in the configuration shown in FIG. 9B may still represent a suitable first configuration 11 within the purposes of the present disclosure.

The detection member of the testing components 7 may comprise optical reading electronics (not shown) adapted to read or interpret the visual information 200 and output enhanced visual information.

In the case of the described testing device, the electronics would be accommodated onboard the testing device 1, for example inside the internal space defined by the main body 3 of the testing device 1. The optical reading electronics would be adapted to read the visual information 200 and produce enhanced visual information such as a colour-coded light confirming or denying a status of pregnancy.

It will be appreciated, however, that the possible different implementations in relation to the type of enhanced visual information used may be numerous. Additionally, the test result may be communicated by appropriate sounds produced by sound-emitting components that may be part of the electronics referred to above. Alternatively, and/or additionally, said electronics may project or display the test result through a suitable user interface such as a display or the like provided on the device 1. Additionally, it may be possible to communicate the test result to an external device (a computer or smart phone, or an external screen) via a communication protocol such as Bluetooth® of the like by means of an appropriate chip In the described arrangement, a window 29 is formed on an upper face 3u of the main body 3 of the device 1 as shown, for example, with reference to FIGS. 2 and 3. The handle 9 is arranged to impede completely sight of the visual information 200 displayed through said window 29 by the detection member of the testing components 7 by overlapping fully with the main body 3 of the device 1 when the handle 9 is in the folded configuration 11 of FIG. 4.

The folded configuration of FIGS. 1 and 4 is a preferred first configuration 11p since in addition it maximises the compactness of the testing device 1. This can be useful for example when packaging the device 1, after assemblage.

It will be appreciated, however, that it is not necessary for the handle to overlap fully with said upper face 3u of the main body 3 of the device 1. Depending on the location and configuration of the window 29 (if one exists) and/or the location of the visual information 200, it may be possible to fully impede sight of the visual information by partially covering the main body 3 of the device and its upper face 3u (if this is where the information 200 is made available) with the reconfigurable handle 9.

It is advantageous for the handle 9 to be arranged in one of said first configurations while simultaneously minimising the space occupied by the testing device 1. Accordingly, at least one of the first configurations 11p has been defined as a preferred first configuration 11p for packaging and therefore storage and/or transportation of the testing device 1. As mentioned above, this preferred configuration 11p of the handle 9 corresponds to a configuration in which the testing device has maximum compactness. This configuration is also shown in FIGS. 1 and 9A of the drawings. The configuration of maximum compactness can be defined as a configuration in which the testing device occupies minimum packaging volume.

FIG. 4 does not show a packaging configuration for the testing device since the protection cap 17 of the testing device 1 has been removed for testing. In other words, the device 1 would normally be packaged with the cap 17 on. FIG. 4, instead, shows the testing device 1 in a configuration suitable for disposing of the same with enhanced privacy procured by the handle 9 being in a suitable first configuration 11 (here corresponding to the preferred first configuration discussed above). The test device 1 can be disposed of with or without reinserting the cap 17. If the device 1 is disposed of without the cap 17, privacy of the test results can still be achieved because the handle 9 now hinders the sight of the test results. This may be an advantage over prior art devices which may require a cap to be reinserted to privately dispose of the test device once the test has been taken.

In the described testing device 1, the handle 9 and the main body 3 are rotatably coupled one to the other. Direct connection of the handle 9 and the main body 3 of the testing device 1 is however not indispensable. For example, said main body 3 and the handle 9 could be coupled via an intermediate one or more coupling members such as a hinge member.

In more detail, in the testing device 1 described herein, the main body 3 and the handle 9 form a hinge 20 without any intermediate members being provided. The hinge 20, as it can best be appreciated from FIGS. 5 and 6, is situated on the proximal end portion 4 of the main body 3 which, when the handle 9 is in the preferred first configuration 11p, is also the proximal end 1p of the testing device 1.

Figures 7A, 7B:
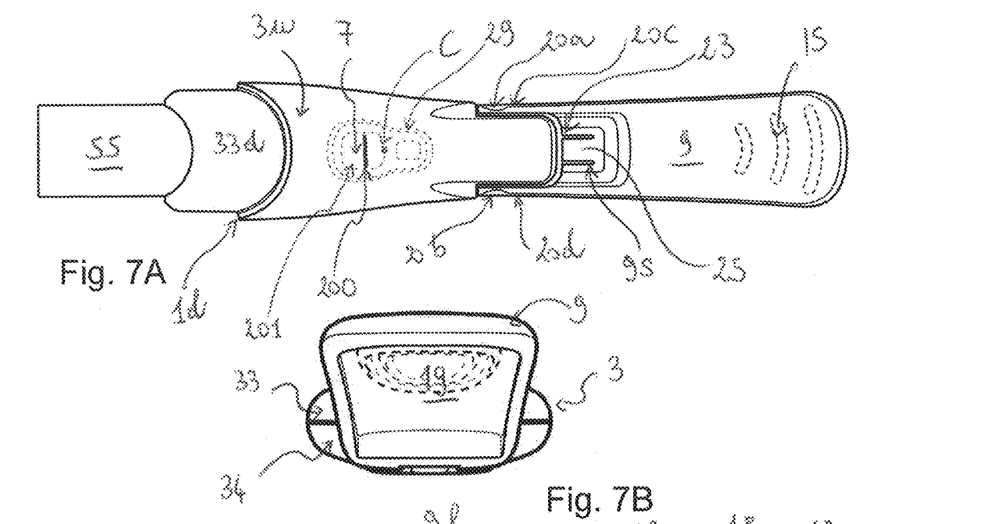
FIG. 7A is a top plan view of the compact testing device in the configuration of FIG. 3.
FIG. 7B is a rear elevation of the compact testing device in the configuration of FIG. 3.
Figure 7C:
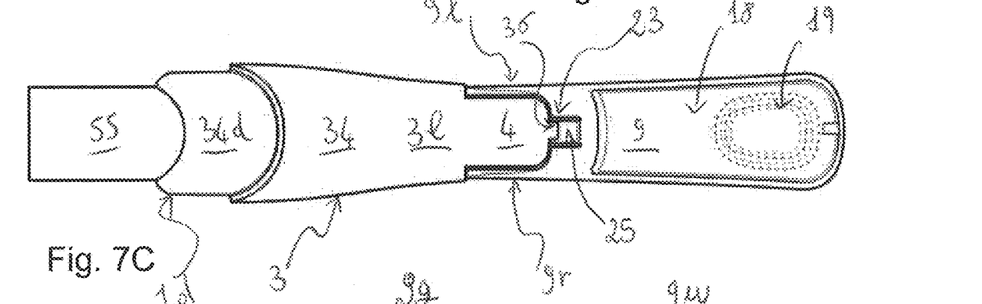
FIG. 7C is a bottom plan view of the compact testing device in the configuration of FIG. 3.

The hinge 20 defines a hinge axis b-b transversal with respect to the main body longitudinal direction a-a, as shown in FIGS. 1, 3 and 7C. The hinge axis b-b lies coplanar with the nominal plane A on which the main body 3 of the testing device 1 generally lies. The hinge 20 and hinge axis b-b are located a distance d inwardly with respect to the proximal edge 4e of the main body 3 of the device 1. Other geometrical solutions for the hinge 20 would however be possible and are within the remit of the skilled person and thus need not further be described or listed here. As an example, the direction b-b may lie outside plane A, be not perfectly parallel with plane A or be alternatively located at the proximal edge 4e or on a rear face 4f of the main body 3.

Constructively, in the described embodiment the hinge 20 is formed by two hinge pins 20a, 20b provided on the main body 3 and protruding laterally/transversally from the proximal end 4 thereof, and corresponding hinge seats 20c, 20d formed on the handle 9, as best seen for example from FIGS. 3, 4, 5 and 6.

Alternative constructions are however possible. For example, it would be possible to couple the handle 9 with the main body 3 via a ball joint.

With the hinge 20 of the present device 1, the handle 9 rotates out-of-pane with respect to plane A around the hinge axis b-b. This is best exemplified by FIGS. 9A-I which show a sequence of angular handle positions between the first, folded configuration 11p of the handle 9 of the testing device 1 (that corresponds to the preferred configuration of maximum packaging compactness) and the second, deployed handle configuration 13 described hereinabove (used by the user for preparing to carry out the test—the next step being that of uncapping the testing device 1 in preparation for the collection of the sample 100). It will be clear, however, that the cap 17 may alternatively be removed at any other time in the sequence shown by FIG. 9.

In one intermediate configuration (the one shown in FIG. 9E), the handle 9 (or, more specifically, the gripping portion 9g of the handle 9) forms with the longitudinal direction a-a and plane A defined by the elongated main body 3 of the device 1 a substantially square angle (90 degrees). In this configuration the handle 9 can be considered as being neither in a first nor in a second configuration as described herein. In this configuration the handle moves freely and is not retained (although this could be provided for, see for example further below the description of a handle retaining mechanism). In the configuration of FIG. 9E, the handle 9 does not, or does not significantly, or usefully, increase the distance between the proximal end of the device 1p and the absorbent wick 55 at the distal end 1d thereof; further, in this configuration, the handle 9 does not significantly hinder the sight of the window 29.

Alternatively (but these embodiments are less preferred and are therefore not described in detail herein) the handle 9 could be slidingly connected to the main body 3 and still perform the required functions in two different configurations: in at least one configuration 11 the handle 9 hinders sight of the visual information 200; and, in another configuration 13 the handle 9 significantly extends the length of the testing device 1. This connection may be via rails, guides or other linear features not described in detail herein.

The testing device 1 described herein in addition incorporates retention means for retaining the handle 9 in the second configuration 13 as depicted in FIGS. 2, 3, 6, 7A-C and 9I. The retention means comprise a handle retaining mechanism 23. The handle retaining mechanism 23 is provided in this instance by an indentation in the form of a slot 24 formed on the proximal end portion 4 of the elongated main body 3 of the testing device 1, together with a protrusion 25 (see for example FIG. 8A) for engaging with said slot 24, situated on the handle 9. The indentation/slot 24 and protrusion 25 are also clearly visible in FIG. 10.

The handle retaining mechanism 23 is adapted to retain the handle 9 in a preferred second configuration 13p that maximises the distance D" described above whilst also providing for balanced handling of the test device 1 for optimal sample collection operations. Accordingly, with the handle 9 in the preferred second configuration 13p the test device 1 does not assume the configuration of a straight testing stick. Due to the slight angle θ (see FIG. 6) formed between the gripping portion 9g of the handle 9 and the longitudinal direction a-a or nominal plane A, the shape of the deployed testing device 1 is more akin to a spoon or is spoon-like, which is an ergonomic and user-friendly configuration for collecting the sample 100, at least for some users.

Figure 9I:
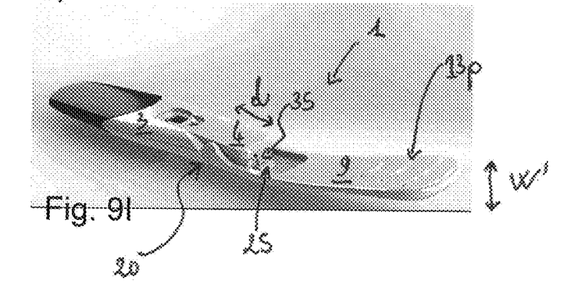

Returning now to the handle retaining mechanism 23, to release the handle 9 from the configuration 13p of, for example, FIG. 9I, after that the test has been carried out, in order to reconfigure the handle 9 to a first configuration 11, a predetermined force is exerted on the handle retaining mechanism 23 to disengage the protrusion 25 from the slot 24 so that the handle 9 can be turned in the backward sequence form the configuration of FIG. 9I to the configuration of FIG. 9A. The handle and main body are in the described embodiment both formed from malleable and/or compliant materials such as, in the present case, plastics.

To withdraw the protrusion 25 of the handle 9 from the slot 24 on the main body 3, the handle 9 is rotated anticlockwise starting from the position shown in FIG. 6 overcoming an initial, resisting moment generated by the coupling between the protrusion 25 and the slot 24. When the initial resisting moment is overcome by a corresponding moment acting in the opposite direction applied by the user to reconfigure the handle 9, the protrusion 25 bends slightly until it disengages from the slot 24 so that the handle 9 can rotate/pivot freely around the hinge 20.

Figure 8A:
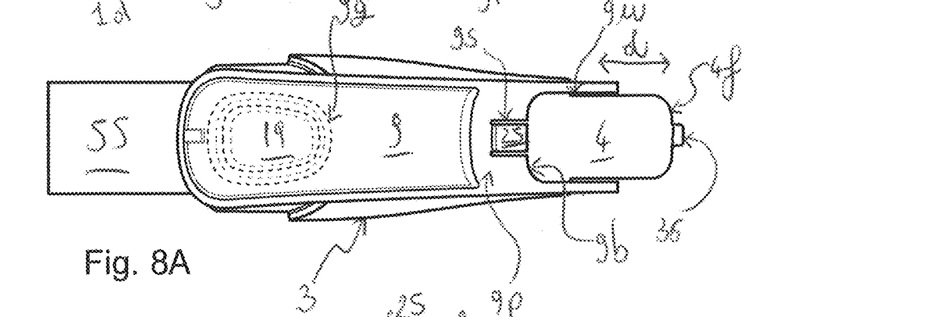
FIG. 8A is a top plan view of the compact testing device in the configuration of FIG. 4.
Figure 8B:
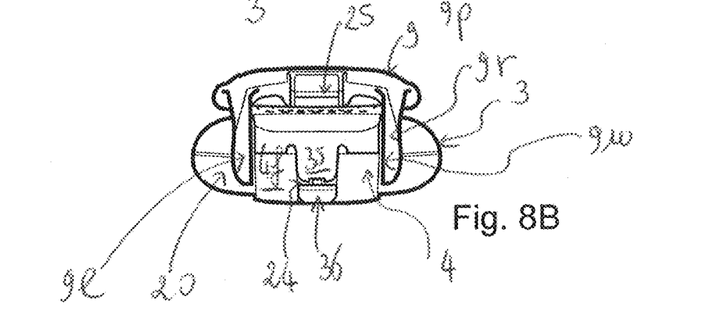
FIG. 8B is a rear elevation of the compact testing device in the configuration of FIG. 4.

In the described embodiment, the protrusion 25 is in the form of a tab or tongue located in the pivoting portion 9p of the handle 9, as best seen in FIG. 7A or FIG. 8B. More specifically, the tab or tongue extends longitudinally from a recess 9s formed on the base 9b of a U-shaped recess 9u formed on the curved pivoting portion 9p of the handle 9. The recess 9s is formed as a cut-away portion on the base 9b of the U-shaped recess 9u of the pivoting portion 9p of the handle 9. The pivoting portion 9p of the handle 9 has left and right legs 9r, 9I that essentially define said U-shaped recess 9u. This U-shaped space 9u, and the location of the hinge 20 along axis b-b, essentially allow the pivoting portion 9p of the handle 9 to clear the proximal end portion 4 of the main body 3 of the testing device 1 when the handle 9 is rotated past it, as shown for example in FIGS. 9G-I.

The slot 24 is essentially an elongated aperture provided on the rear face 4f of the proximal end portion 4 of the main body 3 of the device 1. It is not necessary that this indentation 24 be elongated, and other shapes may likewise be suitable. In the described embodiment, however, the indentation is in the form of a slot 24 which is an elongated gap defined between upper and lower limbs 35, 36 formed on respective shell-like parts 33, 34 that, when coupled, form the main body 3 of the device 1, as it will be further described below.

The upper limb 35 (see for example FIGS. 5, 8B, 9A and 10) extends generally transversally with respect to the longitudinal direction a-a, and parallel to the rear face 4f of the main body 3 of the device 1. The lower limb 36 (see for example also FIGS. 5, 8B, 9A and 10) extends generally parallel with respect to the longitudinal direction a-a, generally as a small protrusion of a lower face 31 of the main body 3 of the device 1.

As can best be appreciated from FIGS. 7C and 10, the lower limb 36 is dimensioned in such a way that the handle cannot be rotated further than the position shown in FIG. 9I, which corresponds to the preferred second configuration 13p of the handle 9 in the described embodiment. The small longitudinal projection in direction a-a of the upper limb 35 (this can best be appreciated from FIGS. 5 and 10) is instead such that the handle 9 can be reconfigured from the position of FIG. 9I into the position of FIGS. 8A and 8B after that the test has been carried out.

As the skilled person will recognise, a variety of alternative handle retaining mechanisms 23 could be implemented, comprising additionally and/or alternatively hole and pin arrangements, straps, elastic bands, magnetic, hook-and-loop coupling features, clips and the like as suitable securing features. These arrangements need not be described in detail herein. However, mention is made of the possibility to incorporate in the handle retaining mechanism locking features for example comprising a key and socket, as slider, a button or the like. These features, for example the key, could then be operated inside the socket to lock or unlock (for example by throwing or withdrawing a respective latch) rotation or an alternative movement of the handle 9 with respect to the body 3 of the testing device 1 for configuring and/or reconfiguring the testing device 1 as required.

In the described compact testing device 1, the handle 9 has approximately the same length of the main body 3 of the testing device 1 (each measuring about 7 cm in length). However, since the hinge 20 is not located at the proximal edge 4e of the proximal end portion 4 of the main body 3 of the device 1 but is slightly inwards therefrom (of around 1 cm), when the handle 9 is folded over the main body 3 the gripping portion 9g of the handle covers a portion of the absorbent wick 55 as shown in FIG. 8A. This is advantageous because with the handle 9 is in the preferred first configuration 11p, which minimises the volume occupied by the device 1, the user is intuitively discouraged from performing the test and is instead intuitively invited to extend the handle 9 before doing so. On another note, the overall length of the handle 9 is instead sufficient to cover the distance between the hinge 20 and the window 29, which in the described device 1 is about 3 cm (with reference to a centre point C of the window 29, as shown in FIG. 7A).

The user will accordingly initially unpack the pregnancy test 1 and dispose it in the configuration shown in FIG. 1. In this configuration, the handle 9 covers a portion of the cap 17 and the user is thus intuitively encouraged to move the handle 9 to the second configuration 13p, which is the one shown in FIGS. 2, 3, 6, &A-C and 9I until the tongue 25 clicks in place in the slot 24. The handle 9 can be freely so reconfigured. At this point, the cap 17 is still on, and it will be clear to the user that the cap 17 needs to be removed in preparation for the test. The handle 9 and the cap 17 thus cooperate in providing intuitive visual instructions to the user as to how best to operate the testing device 1, at least during the initial steps upon unpackaging the device 1, and in preparation for testing.

The device 1 is successively handled by the user to collect the sample 100 in the configuration shown in FIGS. 3 and 7A-C, ie with the handle 9 extended and the cap 17 removed. The gripping portion 9g of the handle 9 at this point does not form a 180 degrees angle with the longitudinal direction a-a of the main body 3 of the device 1; it instead forms an angle of about 15 degrees as shown in FIG. 6. This angle, even at different inclinations, warrants an improved manoeuvrability of the testing device 1 during sample collection. This angle can vary, however, and in some embodiments could be a 180 degrees angle, corresponding to a straight, non-inclined test device in the extended position.

The test is then performed, and the visual information 200 is generated by the testing components 7. The testing device 1 can now be stored or disposed of. To organise that action, the user exercises a counter moment on the handle retaining mechanism 23 to release the handle 9. The now freely rotating handle 9 then folds in the first configuration 11p shown in FIG. 4. The handle 9 is not retained in this position, but it would be straightforward, based on the teachings herein, for the skilled person to implement a further handle retaining mechanism to do this. The user can at this point decide to dispose of the device 1 with increased assurance that the test will remain private.

The test could be different than a pregnancy test. For example, it could be a saliva test to identify a predetermined patient medical condition, or it could be a blood test. In these tests, but also in principle in a pregnancy test, the testing device may be not disposable. Instead, the sample collection element 5 and the testing components 7 could be disposable and replaceable. Depending on the circumstances, the user could therefore decide to apply or re-apply the cap 17 to store the testing device for further or future use.

In a disposable testing device 1 such as the one described herein, the sample collection element 5 and the testing components 7 are permanently mounted within the main body 3 and can be used only once.

The main body 3 is a two-part component formed by the aforementioned upper and lower shell-like parts 33, 34, which, in this case, are made of a plastic material. In this embodiment, these two parts 33, 34 are manufactured separately using an injection moulding technique and have complementary inner surface features (not described herein in detail) which permit the assemblage thereof to form the main body 3.

Each of the hinge pins 20a, 20b is formed by two halves each formed integrally with a respective shell-like part 33, 34.

The sample collection element 5 is sandwiched between distal ends 33d, 34d of said upper and lower parts 33, 34 and the one or more testing components 7 are accommodated within the space defined between internal surfaces of said upper and lower parts 33, 34.

The testing device 1 described herein can be provided as a kit 1001 of assemblable parts. The list of the parts for this kit 1001 is as follows:

Shell-like upper part 33;
Shell-like lower part 34;
Optional environment conditioning disc (not shown) for incorporation on the lower part 34 of the main body 3, inside the testing device 1;
Absorbent wick 55;
Transversal anti-flood sample retention member (not shown) for incorporation on the upper part 33 of the main body 3 of the testing device, also inside the testing device 1;
Testing components 7, comprising:
  a porous strip with coloured dried particulate labels for fluid communication with the absorbent wick 55;
  a backing strip for adhesively connecting at one end and on one face to the porous strip and at the opposite end and on the same face to a test strip (or, detection member, as described above) having transversal test lines for intercepting any reacted labels provided on the analyte detection zone 201;

a test strip/detection member, as hereinabove described; and, a reference element containing one or more control lines for informing whether the test has been successfully taken despite the absence of the hCG hormone in the sample;

Handle 9; and

Cap 17.

In the description here above, the following reference numerals have been used and are below listed:

1: compact testing device
1*d*: distal end of the compact testing device
1*p*: proximal end the compact testing device
3: main body of the compact testing device
3*u*: upper face of the main body
31: lower face of the main body
4: proximal end portion of the main body
4*e*: proximal edge of the proximal end portion of the main body
4*f*: rear face of the main body
5: sample collection element
55: absorbent wick
7: testing components
9: reconfigurable handle
9*g*: gripping portion of reconfigurable handle
9*p*: pivoting portion of reconfigurable handle
9*u*: U-shaped recess of pivoting portion of reconfigurable handle
9*r*, 9*l*: legs of reconfigurable handle
9*b*: base of U-shaped recess of pivoting portion of reconfigurable handle
9*s*: recess formed on above base
11: first configuration of handle
13: second configuration of handle
11*p*: preferred first configuration of handle (maximises compactness)
13*p*: preferred second configuration of handle (maximises ergonomics)
15: ridges on inner face of reconfigurable handle
16: inner face of reconfigurable handle
17: cap
18: outer face of reconfigurable handle
19: annular gripping elements
20: hinge
20*a*, 20*b*: hinge pins
20*c*, 20*d*: hinge seats
23: handle retaining mechanism
24: slot
25: protrusion or tongue/tab (located on handle)
29: window
33: upper shell-like part of main body
33*d*: distal end of upper shell-like part of main body
34: lower shell-like part of main body
34*d*: distal end of lower shell-like part of main body
35: upper limb (located on upper shell-like part of main body)
36: lower limb (located on lower shell-like part of main body)
100: sample
200: visual information
201: analyte detection zone
1001: kit In the description above, the following reference letters and symbols have been used and are listed below:

o: vertical offset
A: plane
a-a: longitudinal direction
b-b: hinge axis, transversal direction
d: inward offset of hinge 20
D': distance of absorbent wick from proximal end of device at handle closed
D": distance of absorbent wick from proximal end of device at handle closed at handle open
W: maximum width of device 1 in the packaging configuration
W': maximum width of device 1 in the preferred second configuration
W": maximum width of device 1 in an alternative second configuration
C: centre of window One or more embodiments of the present invention have been described above in a non-limiting manner purely to enable the skilled person to carry out the invention across a range of embodiments. Accordingly, protection is sought within the scope of the following claims.

What is claimed is:

1. A testing device comprising:
    a main body adapted to support a sample collection element for collecting a sample, said sample collection element being supported at a distal end of the testing device and being in communication with one or more testing components provided within said main body for producing visual information related to said sample;
    a removable cap for protecting the sample collection element, wherein the main body is adapted to support the removable cap; and
    a handle reconfigurable with respect to said main body and said removable cap when the removable cap is supported on said main body, such that in a first handle configuration the handle hinders sight of the visual information, and in a second handle configuration the handle facilitates the collection of said sample by increasing a distance between a proximal end of the testing device and the sample collection element, wherein the handle and the main body are rotatably moveable relative to each other, the main body and the handle are connected via a hinge, and the hinge defines a hinge axis transversal with respect to the main body; wherein the testing device is adapted such that the handle is reconfigurable from said second handle configuration to said first handle configuration to hinder sight of the visual information after testing has been carried out.

2. The testing device of claim 1, wherein the main body is elongated and defines a longitudinal direction, and wherein the sample collection element and the one or more testing components are spaced along said longitudinal direction.

3. The testing device of claim 2, wherein the handle extends in the longitudinal direction in at least one of the first handle configuration and/or the second handle configuration.

4. The testing device of claim 1, wherein the sample collection element comprises an absorbent wick.

5. The testing device of claim 1, wherein, in said first handle configuration, the handle impedes sight of said visual information.

6. The testing device of claim 5, wherein, in said first handle configuration, the handle overlaps with the main body.

7. The testing device of claim 1, wherein the main body comprises one or more hinge pins and the handle comprises one or more associated hinge seats for receiving said hinge pins, or vice versa; or
wherein the hinge comprises a hinge member distinct from the main body and the handle of the testing device.

8. The testing device of claim 1, further comprising a retention means for retaining the handle in said first handle configuration and/or said second handle configuration.

9. The testing device of claim 8, wherein said retention means comprise one or more locking and/or unlocking features for locking and/or unlocking the handle in the first handle configuration and/or the second handle configuration.

10. The testing device of claim 1, wherein the handle is reconfigurable with respect to said main body in said first handle configuration to discourage or at least partially obstruct collection of said sample.

11. The testing device of claim 1, wherein the testing device is a lateral-flow testing device.

12. A disposable testing device comprising a testing device according to claim 1, wherein the sample collection element and the one or more testing components are permanently mounted to, within or on said main body.

13. A kit of assemblable parts for forming a testing device according to claim 1 or a disposable testing device according to claim 12.

14. A method of testing a sample, the method comprising: providing a testing device comprising:
a main body adapted to support a sample collection element for collecting a sample, said sample collection element being supported at a distal end of the testing device and being in communication with one or more testing components provided within said main body for producing visual information related to said sample, thereby informing a user of an outcome of a test,
a removable cap for protecting the sample collection element, wherein the main body is adapted to support the removable cap; and,
a handle reconfigurable with respect to said main body and said removable cap when the removable cap is supported on said main body, such that in a first handle configuration the handle hinders sight of the visual information, and in a second handle configuration the handle facilitates the collection of said sample by increasing a distance between a proximal end of the testing device and the sample collection element, wherein the handle and the main body are rotatably moveable relative to each other, the main body and the handle are connected via a hinge, and the hinge defines a hinge axis transversal with respect to the main body;
moving the handle to a second handle configuration in preparation for carrying out said testing;
collecting a sample;
moving the handle to a first handle configuration to hinder sight of the visual information after testing has been carried out.

15. The method of claim 14, wherein moving the handle to said first and/or second configurations comprises rotating the handle with respect to the main body of the testing device.

16. The method of claim 14, wherein the method further comprises:
overcoming retention means for retaining the handle in said second configuration.

17. The testing device of claim 2, wherein the sample collection element and the one or more testing components are adjacent.

18. The testing device of claim 6, wherein:
the main body defines a window for displaying said visual information and, in said first handle configuration, the handle fully overlaps said window; and/or
said first handle configuration is a predetermined handle configuration that maximizes compactness of the testing device for storage, transportation and/or disposal.

19. The testing device of claim 1, wherein:
the hinge is located at a proximal end portion of the main body; and/or
the hinge is offset a distance inwardly with respect to a rear face of the proximal end portion of the main body of the device.

20. The testing device of claim 1, wherein:
said hinge axis lies coplanar with a nominal plane on which the main body generally lies.

21. The testing device of claim 8, wherein:
the retention means comprise cooperating retaining features provided, respectively, on the main body and on the handle;
said retention means comprise an indentation defined on a rear face of the proximal end portion of said main body and a protrusion for engaging with said indentation, said protrusion being formed on said handle; and/or
said retention means are adapted to release the handle for reconfiguration when a predetermined force is exerted on said retention means.

22. The testing device of claim 1, wherein:
a length of said handle is greater than or at least substantially equal to a distance between said hinge and said sample collection element.

23. The testing device of claim 1, wherein:
in said first handle configuration, the handle at least partially overlaps the cap.

24. The testing device of claim 11, wherein:
the collection element is in fluid communication with the one or more testing components via a flow path;
the one or more testing components comprise an analyte detection zone for locally detecting analytes contained in said sample;
the one or more testing components comprise mobilizable dried particulate labels for bindingly reacting with said analytes;
said sample is urine; and/or
said testing device is a pregnancy and/or ovulation and/or menopause testing device.

25. The disposable testing device of claim 12, wherein:
the main body is a monolithic component; or
the main body is a two-part component, comprising upper and lower shell-like parts, made of a plastic material, wherein the sample collection element is sandwiched between said upper and lower parts and the one or more testing components are accommodated within a space defined by said upper and lower parts.

26. The method of claim 15, wherein said rotating is in an out-of-plane direction with respect to a plane over which the main body of the device lies.

27. The method of claim 16, further comprising:
reconfiguring the handle to said first configuration.

28. The method of claim 16, wherein in said first configuration the handle at least partially overlaps the cap.

* * * * *